United States Patent [19]

Keller et al.

[11] Patent Number: 4,765,328
[45] Date of Patent: Aug. 23, 1988

[54] SURGICAL INSTRUMENT HANDLE COUPLING

[75] Inventors: Philip J. Keller, Pompton Plains; Robert C. Cohen, Denville, both of N.J.

[73] Assignee: Osteonics Corp., Allendale, N.J.

[21] Appl. No.: 83,483

[22] Filed: Aug. 10, 1987

[51] Int. Cl.⁴ ............................................. A61F 17/32
[52] U.S. Cl. .................................. 128/303 R; 623/18; 623/23
[58] Field of Search ................. 128/303, 303 R, 92 R, 128/92 VT, 92 VW, 92 VY; 623/18, 23, 66, 20, 22, 18

[56] References Cited

U.S. PATENT DOCUMENTS

| | | | |
|---|---|---|---|
| 3,955,568 | 5/1976 | Neufeld | 128/92 VT |
| 4,065,816 | 1/1978 | Sawyer | 128/303 R |
| 4,124,026 | 11/1978 | Berner et al. | 128/303 R |
| 4,135,517 | 1/1979 | Reale | 128/303 R |
| 4,601,289 | 7/1986 | Chiarizzio et al. | 623/23 |
| 4,634,444 | 1/1987 | Noiles | 623/20 |
| 4,642,121 | 2/1987 | Keller | 623/18 |

Primary Examiner—Raymond A. Nelli
Attorney, Agent, or Firm—Samuelson & Jacob

[57] ABSTRACT

A coupling arrangement for selectively coupling and uncoupling the handle and the blade of a surgical instrument, such as a broach, includes a key projecting axially from the handle and receivable within a first recess portion in the blade to engage locking pins upon transverse movement of the key into locking engagement with the locking pins, and a plunger selectively movable into a further recess portion contiguous with the key for precluding relative movement of the handle and the blade in the transverse direction so as to maintain the key in locking engagement, the plunger being selectively retractable from the further recess portion to permit relative transverse movement of the handle and the blade, and consequent movement of the key out of locking engagement with the locking pins, to enable uncoupling of the handle from the blade.

15 Claims, 2 Drawing Sheets

SURGICAL INSTRUMENT HANDLE COUPLING

The present invention relates generally to surgical instruments and pertains, more specifically, to surgical instruments used in connection with the implant of prosthetic joints.

The use of prosthetic implants to replace the natural joints of the body, either as a result of disease or injury to the natural joint, is becoming more and more commonplace. For example, in the replacement of a hip joint, it is very often necessary to replace the natural femoral head with a prosthetic stem which enters the femur and provides an accurately located and securely held prosthetic head in place of the natural femoral head. The procedures for implanting a prosthetic stem include the use of a broach or rasp, usually as the last step in preparing the proximal femoral shaft for the reception of the prosthetic stem. The purpose of the broach or rasp is to provide precise contouring of the proximal femoral shaft to the gross geometry of the prosthetic stem, thereby assuring accurate location and precise fit. The configuration of the broach or rasp is made to emulate that of the prosthetic stem to enable the attainment of the desired precision. In order to facilitate precise utilization of the broach or rasp, it has been suggested that the handle of the instrument be selectively detachable from the blade so that the location of the blade within the femoral shaft can be gauged precisely and used as a means for determining the subsequent accurate location of the prosthetic stem.

The present invention provides a coupling arrangement which enables effective selective attachment and detachment of the handle and the blade of a surgical instrument, such as a broach, for attaining the above result, and provides several objects and advantages, some of which may be summarized as: strength and rigidity in the connection between the blade and the handle for accuracy and precision in the use of the broach; ease of attachment or detachment, as desired, for facilitating the use of the detachable handle feature under the conditions encountered during a surgical procedure, and, in particular, enabling the quick and reliable attachment or detachment necessary under operating room conditions; simplicity in the number and the configuration of the component parts of the arrangement for enabling ease of maintenance as well as use; compliance with all of the requirements for surgical instruments insofar as materials and construction necessary to serve in the surgical environment; ease of use in the attainment of the appropriate alignment, location and fit in the implant of the prosthetic component; and rugged construction for reliable service over an extended service life.

The above objects and advantages, as well as further objects and advantages, are attained by the present invention which may be described briefly as a coupling arrangement for use in the selective coupling and uncoupling of the handle and the blade of an axially extending surgical instrument, such as a broach, during a procedure for implanting a prosthetic implant component, the coupling arrangement comprising: a proximal surface extending transversely along the blade; a mating surface extending transversely along the handle, the mating surface essentially matching the proximal surface of the blade when the blade and the handle are coupled; a key extending in a first direction from one of the proximal and mating surfaces toward the other of the proximal and mating surfaces; a first recess in the corresponding one of the handle and the blade for receiving the key when the blade and the handle are moved along a second direction transverse to the first direction into coupled position; interengagable locking means on the key and in the cavity for interengaging in response to relative movement of the handle and the blade along the second direction into the coupled position to secure the handle and the blade against relative movement in the first direction; a second recess in the blade, the second recess extending generally in the first direction; a plunger carried by the handle and movable therein selectively between a first position wherein the plunger extends beyond the proximal and mating surfaces and into the second recess to preclude relative movement between the handle and the blade along the second direction, and a second position wherein the plunger is retracted from the second recess to permit such relative movement; and actuator means for moving the plunger selectively between the first and second positions thereof, thereby enabling selective coupling and uncoupling of the handle and the blade.

The invention will be understood more fully, while still further objects and advantages will become apparent, in the following detailed description of a preferred embodiment of the invention illustrated in the accompanying drawing, in which.

Figure 1:
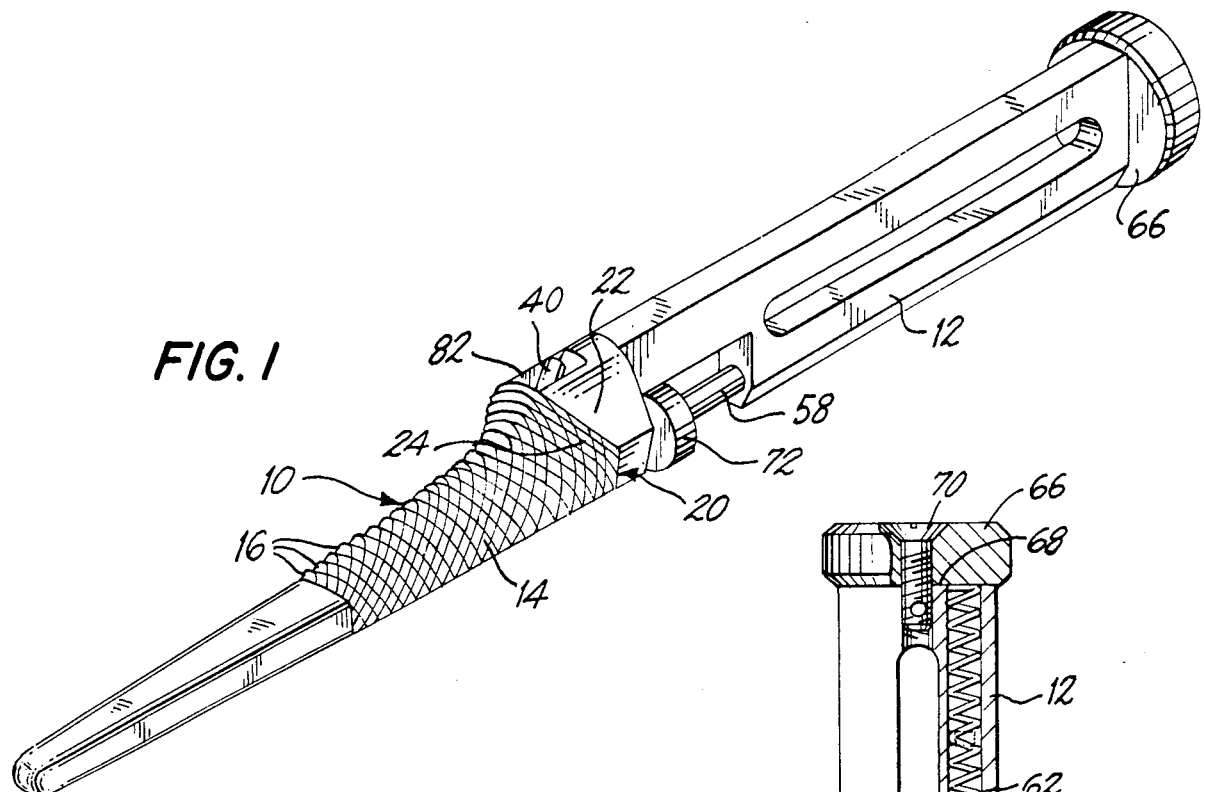
FIG. 1 is a perspective view of a broach with the handle and blade attached.

Referring now to the drawing, and especially to FIG. 1 thereof, a surgical instrument is illustrated in the form of a broach 10 and is seen to include a handle 12 and a blade 14. Handle 12 has an overall configuration which is contoured to fit comfortably within the hand of a surgeon who will manipulate the blade 14 within a reamed passage in the proximal femoral shaft, during an implant procedure, to conform the passage to a configuration which will receive a prosthetic femoral stem in an accurate location and in a precise fit within the femur. Thus, the blade 14 has an overall contour configuration which essentially emulates the configuration of the femoral stem to be implanted, and includes a plurality of broach teeth 16 for accomplishing the desired result.

Figure 3:
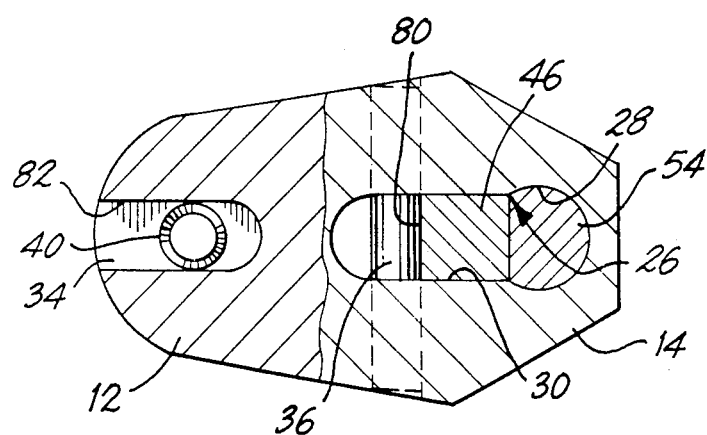
FIG. 3 is a lateral cross-sectional view taken along line 3—3 of FIG. 2.
Figure 2:
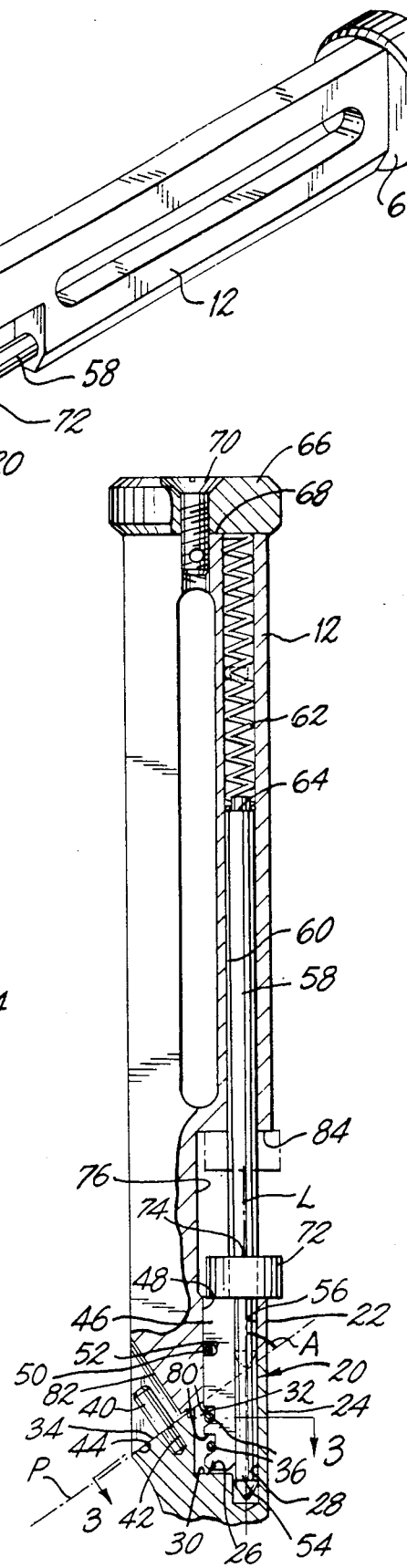
FIG. 2 is an enlarged, fragmentary cross-sectional view of a portion of FIG. 1, showing the coupling arrangement of the present invention.

Turning now to FIGS. 2 and 3, as well as to FIG. 1, handle 12 and blade 14 are coupled together by coupling means shown in the form of coupling arrangement 20 located in the lower end 22 of the handle 12 and the proximal end 24 of the blade 14. The proximal end 24 of the blade 14 includes a cavity 26 having cylindrical recess portion 28 and a keyway portion 30 which has a generally rectangular cross-sectional configuration. Cavity 26 has an open mouth 32 at the proximal surface 34 of the blade 12, which proximal surface 34 extends in a direction generally along a plane P placed at an angle A to the longitudinal axis L of the assembled handle 12 and blade 14. While proximal surface 34 is illustrated as being flat and planar, other surface configurations may be incorporated into proximal surface 34. A pair of locking pins 36 are anchored in the blade 14, at either side of the keyway portion 30, and extend laterally across the cavity 26 to straddle the keyway portion 30, as best seen in FIG. 3. A post 40 is anchored in the blade 14 at 42 and projects from the proximal surface 34 in an upward direction generally perpendicular to plane P, for purposes which will be described in further detail below.

A mating surface 44 extends along the lower end 22 of the handle 12 and matches the configuration of the proximal surface 34 of the blade 14 so as to resist relative movement between the handle 12 and the blade 14 upon axial downward movement of broach 10 during broaching. A key 46 is seated within a channel 48 in the handle 12, at the lower end 22 thereof, and projects axially downwardly from the mating surface 44. A transverse pin 50 is affixed within the handle 12 and passes through a complementary slot 52 in key 46 to secure the key 46 against axial movements relative to the handle 12, once the key 46 is seated properly in the complementary channel 48. An axially-oriented plunger 54 is received within a complementary lower bore 56 in the handle 12 for sliding movement in axially upward and downward directions. Plunger 54 is an integral part of, and preferably is unitary with, an axial shaft 58 which slides within a complementary upper bore 60 in handle 12. A helical spring 62 is placed within the upper bore 60, between the upper end 64 of the shaft 58 and an end pad 66 affixed to the upper end 68 of the handle 12, as by a threaded fastener 70. Helical spring 62 biases the shaft 58 and plunger 54 axially downwardly, until a collar 72, which is affixed to shaft 58 is seated against a lower shoulder 74 which lies along the lowermost boundary of a recess 76 in the handle 12. In this lower position of shaft 58, and plunger 54, the plunger 54 is coextensive with the key 46, as shown in FIG. 2. Key 46 includes a pair of locking notches 80 (also see FIG. 4) corresponding to the pair of locking pins 36 and engaged with the locking pins 36 to retain the key 46 within the keyway portion 30 of cavity 26 in the blade 14. At the same time post 40 is received within a complementary groove 82 in the handle 12. Thus, the engagement of the key 46 with the locking pins 30 secures the handle 12 against axial movement relative to the blade 14, especially upon upward movement of the broach 10 during withdrawal of the blade 14 from a broached passage, while the engagement of the post 40 within groove 82 reinforces the coupling of the handle 12 and the blade 14 against relative twisting about the longitudinal axis L.

Figures 4, 5:
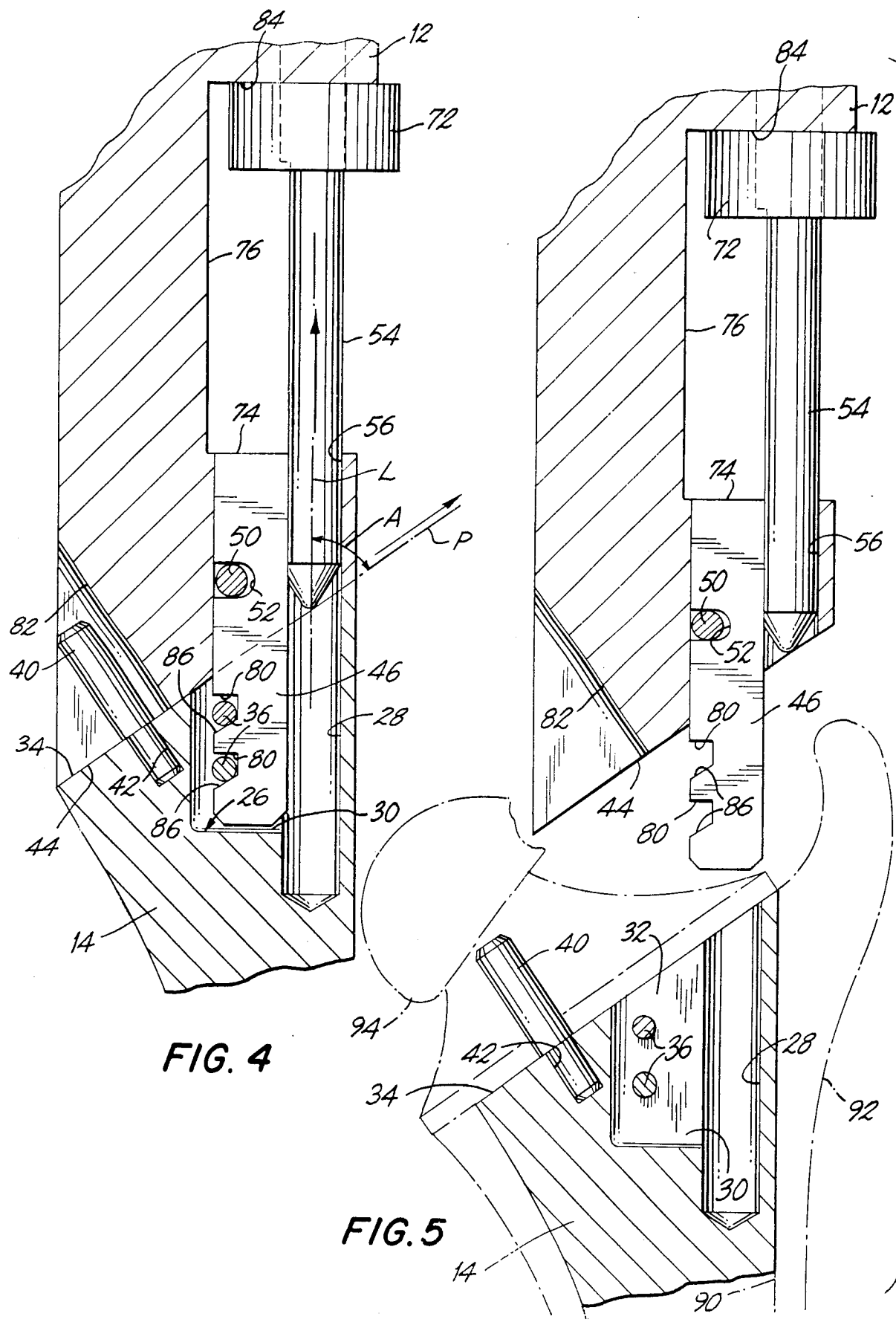
FIG. 4 is a cross-sectional view similar to FIG. 2, but with the component parts in another operating position.
FIG. 5 is a view similar to FIG. 4, but with the component parts in still another operating position.

When it is desired to uncouple the handle 12 and blade 14, the collar 72 merely is displaced axially upwardly, as seen in FIG. 4, until the collar 72 abuts an upper shoulder 84 which is located along the uppermost boundary of recess 76 in handle 12, to retract shaft 58 and withdraw plunger 54 from the cylindrical recess portion 28. Upon such withdrawal of the plunger 54 relative sliding motion is permitted between the handle 12 and the blade 14, along the complementary proximal surface 34 and mating surface 44, in the direction indicated by the arrow in FIG. 4, until the locking notches 80 of key 46 clear the locking pins 36 in blade 14, and relative axial movement is permitted between the handle 12 and the blade 14 for complete detachment, as illustrated in FIG. 5. In this connection, it is noted that the lower boundaries 86 of locking notches 80 are angled at the same angle A to the axis L as are the proximal surface 34 and the mating surface 44, so that the sliding movement in the direction of the arrow is permitted once the plunger 54 is withdrawn from the cylindrical recess portion 28.

Since the overall contour configuration of the blade 14 emulates the configuration of the corresponding portion of the prosthetic femoral stem component to be implanted, the coupling arrangement 20 enables accurate determination of completion of the passage within which the femoral stem component will be received. Thus, as the surgeon approaches completion of the broaching step, the blade 14 may be fitted into the broached passage, shown in phantom at 90 in FIG. 5 in the proximal femoral shaft illustrated in phantom at 92, and the handle 12 may be detached, leaving the blade 14 seated in the passage 90. The placement and orientation of the proximal surface 34 of the blade 14 may be observed as a gauge of the accuracy of the elevation of the broached passage 90. Further, post 40 is positioned relative to proximal surface 34 so that the post 40 may be employed for the placement of a trial femoral neck and head, shown in phantom at 94, on the post 40 for gauging the position of the actual prosthetic femoral head upon completion of the implant. In this manner, the coupling arrangement 20 enables the surgeon to conduct trials readily during the implant procedure, without the necessity for using actual prosthetic components for such trials and without compromising the integrity of the connection between the handle 12 and the blade 14, while maintaining ease and rapidity of selective connection and disconnection during the broaching stages of the procedure.

It will be seen that the coupling arrangement of the present invention provides a surgical instrument, such as a broach, of improved utility and flexibility. In the implant of a prosthetic femoral stem, the procedure is expedited by facilitating the determination of the progress and completion of the broaching step, without reducing the strength and rigidity of the connection between the handle and the blade of the broach, or the ability to selectively connect or disconnect with ease and rapidity. Simplicity is maintained without diminution of rugged construction and appropriate materials.

It is to be understood that the above detailed description of an embodiment of the invention is provided by way of example only. Various details of design and construction may be modified without departing from the true spirit and scope of the invention as set forth in the appended claims.

The embodiments of the invention in which an exclusive property or privilege is claimed are defined as follows:

1. A coupling arrangement for use in the selective coupling and uncoupling of the handle and the blade of an axially extending surgical instrument, such as a broach, during a procedure for implanting a prosthetic implant component, the coupling arrangement comprising:
   a proximal surface extending transversely along the blade;
   a mating surface extending transversely along the handle, the mating surface essentially matching the proximal surface of the blade when the blade and the handle are coupled;
   a key extending in a first direction from one of said proximal and mating surfaces toward the other of said proximal and mating surfaces;

a first recess in the corresponding one of said handle and said blade for receiving the key when the blade and the handle are moved along a second direction transverse to the first direction into coupled position;

interengagable locking means on the key and in the cavity for interengaging in response to relative movement of the handle and the blade along the second direction into the coupled position to secure the handle and the blade against relative movement in the first direction;

a second recess in the blade, the second recess extending generally in the first direction;

a plunger carried by the handle and movable therein selectively between a first position wherein the plunger extends beyond the proximal and mating surfaces and into the second recess to preclude relative movement between the handle and the blade along the second direction, and a second position wherein the plunger is retracted from the second recess to permit said relative movement; and actuator means for moving the plunger selectively between the first and second positions thereof, thereby enabling selective coupling and uncoupling of the handle and the blade.

2. The invention of claim 1 wherein the key projects from the handle and the first recess is located in the blade.

3. The invention of claim 2 wherein the first recess and the second recess are contiguous with one another.

4. The invention of claim 3 wherein the key and the plunger extend in parallel directions.

5. The invention of claim 4 wherein the key and the plunger extend in the axial direction.

6. The invention of claim 5 including biasing means for biasing the plunger toward the first position.

7. The invention of claim 1 including a post projecting from one of said proximal surface and said mating surface, and a groove in the other of said proximal surface and said mating surface for receiving the post when the handle and the blade are coupled.

8. The invention of claim 1 wherein the post projects from the proximal surface of the blade, normal to the proximal surface, for the reception of a trial prosthetic implant component upon uncoupling of the handle from the blade.

9. The invention of claim 8 wherein the proximal surface extends at an acute angle to the axial direction.

10. The invention of claim 9 wherein the key is spaced transversely from the post and extends in a generally axial direction.

11. The invention of claim 10 wherein the key projects from the handle and the first recess is located in the blade.

12. The invention of claim 11 wherein the first recess and the second recess are contiguous with one another.

13. The invention of claim 12 wherein the key and the plunger extend in parallel directions.

14. The invention of claim 13 wherein the key and the plunger extend in the axial direction.

15. The invention of claim 14 including biasing means for biasing the plunger toward the first direction.

* * * * *